US011881312B2

(12) United States Patent
Murozono et al.

(10) Patent No.: US 11,881,312 B2
(45) Date of Patent: Jan. 23, 2024

(54) VITAL SIGN INFORMATION SENSOR AND VITAL SIGN INFORMATION DISPLAY SYSTEM

(71) Applicant: NIHON KOHDEN CORPORATION, Tokyo (JP)

(72) Inventors: Tomomi Murozono, Tokorozawa (JP); Makiko Fumoto, Tokorozawa (JP); Hideki Fujisaki, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 94 days.

(21) Appl. No.: 17/040,133

(22) PCT Filed: Mar. 27, 2019

(86) PCT No.: PCT/JP2019/013249
§ 371 (c)(1),
(2) Date: Sep. 22, 2020

(87) PCT Pub. No.: WO2019/189391
PCT Pub. Date: Oct. 3, 2019

(65) Prior Publication Data
US 2021/0074433 A1    Mar. 11, 2021

(30) Foreign Application Priority Data
Mar. 29, 2018 (JP) ................. 2018-064878

(51) Int. Cl.
*G16H 50/30* (2018.01)
*G16H 40/63* (2018.01)
(Continued)

(52) U.S. Cl.
CPC ......... *G16H 50/30* (2018.01); *A61B 5/14551* (2013.01); *A61B 5/742* (2013.01); *G16H 40/63* (2018.01)

(58) Field of Classification Search
CPC ........ G16H 50/30; G16H 40/63; G16H 40/40; G16H 50/20; A61B 5/14551; A61B 5/742
See application file for complete search history.

(56) References Cited

U.S. PATENT DOCUMENTS 7,865,223 B1    1/2011  Bernreuter
2004/0083427 A1  4/2004  Wada
(Continued)

FOREIGN PATENT DOCUMENTS

JP    7-236625 A    9/1995
JP   2008-532680 A   8/2008
(Continued)

OTHER PUBLICATIONS

"University of Iowa Health Care, Pulse Oximetry Basic Principles and Interpretation, Oct. 3, 2017, https://medicine.uiowa.edu/iowaprotocols/pulse-oximetry-basic-principles-and-interpretation" (Year: 2017).*
(Continued)

Primary Examiner — Joseph M Dietrich
Assistant Examiner — Michael T. Holtzclaw
(74) Attorney, Agent, or Firm — Sughrue Mion, PLLC

(57) ABSTRACT

A vital sign information sensor for acquiring vital sign information from a physiological tissue of a subject includes: a sensor element configured to acquire the vital sign information from the subject; and a memory storing URI information. The URI information is capable of gaining access to an electronic content provided by a WEB server disposed on a communication network. When the vital sign information sensor is communicably connected to a vital sign information display apparatus, the URI information is transmitted from the memory to the vital sign information display apparatus. The electronic content includes information relevant to the vital sign information sensor.

10 Claims, 4 Drawing Sheets

(51) Int. Cl.
*A61B 5/1455* (2006.01)
*A61B 5/00* (2006.01)

(56) References Cited

U.S. PATENT DOCUMENTS

| | | |
|---|---|---|
| 2008/0015424 A1 | 1/2008 | Bernreuter |
| 2008/0214906 A1 | 9/2008 | Wang et al. |
| 2011/0060200 A1 | 3/2011 | Bernreuter |
| 2012/0059911 A1 | 3/2012 | Randhawa et al. |
| 2012/0190946 A1 | 7/2012 | Bernreuter |
| 2014/0081100 A1* | 3/2014 | Muhsin ............... A61B 5/318 600/323 |
| 2014/0249390 A1 | 9/2014 | Bernreuter |
| 2016/0188824 A1* | 6/2016 | Geleijnse ............. G16H 40/63 705/2 |
| 2017/0035334 A1 | 2/2017 | Bernreuter |

FOREIGN PATENT DOCUMENTS

| | | | | |
|---|---|---|---|---|
| JP | 2012-53890 A | | 3/2012 | |
| JP | 2012053890 A | * | 3/2012 | ....... G06F 17/30876 |
| JP | 2017076245 A | * | 4/2017 | |
| WO | WO-2018152410 A1 | * | 8/2018 | ............. G06F 16/00 |

OTHER PUBLICATIONS

International Search Report dated Jun. 26, 2019 (PCT/ISA/210) issued by the International Searching Authority for International Application No. PCT/JP2019/013249.

Written Opinion dated Jun. 26, 2019 (PCT/ISA/237) issued by the International Searching Authority for International Application No. PCT/JP2019/013249.

Communication dated Apr. 5, 2022 by the Japanese Patent Office in Japanese Patent Application No. 2018-064878.

Communication dated Oct. 11, 2022 by the Japanese Patent Office in Japanese Patent Application No. 2018-064878.

* cited by examiner

VITAL SIGN INFORMATION SENSOR AND VITAL SIGN INFORMATION DISPLAY SYSTEM

TECHNICAL FIELD

The present disclosure relates to a vital sign information sensor and a vital sign information display system.

BACKGROUND ART

A pulse oximeter which can measure vital sign information (e.g. arterial oxygen saturation (SpO2), a pulse rate, etc.) of a subject (e.g., patient) using a probe mounted on a finger etc. of the subject has been disclosed (e.g., see JP-A-7-236625). According to the disclosure of JP-A-7-236625, the probe provided with a light emitter and a light receiver is mounted on the finger of the subject, so that the vital sign information of the subject can be acquired based on an electric signal acquired from the light receiver.

When a medical worker who does not have much experience in using a vital sign information sensor such as the pulse oximeter uses the vital sign information sensor, it is conceived that the medical worker may have to refer to an operating method of the vital sign information sensor, specifications of the vital sign information sensor, or a treatment status etc. of the subject. In this point, prints about an operating manual of the vital sign information sensor or specifications of the vital sign information sensor are heretofore attached to the vital sign information sensor when the vital sign information sensor is purchased. To use the vital sign information sensor, the medical worker may require time or labor to search for the prints if he or she does not know where the prints of the operating manual etc. are stored. Further, it can be also anticipated that the medical worker may have lost the prints.

In such a case, there is a possibility that the medical worker cannot perform proper diagnosis using the vital sign information sensor. Thus, there is still room to further improve usability of the vital sign information sensor in terms of information relevant to the vital sign information sensor such as the operating manual etc. of the vital sign information sensor.

SUMMARY

The present disclosure provides a vital sign information sensor whose usability is improved and a vital sign information display system.

According to one or more aspects of the present disclosure, there is provided a vital sign information sensor for acquiring vital sign information from a physiological tissue of a subject.

The sensor comprises:
- a sensor element configured to acquire the vital sign information from the subject; and
- a memory storing URI information, wherein the URI information is capable of gaining access to an electronic content provided by as WEB server disposed on a communication network.

When the vital sign information sensor is communicably connected to a vital sign information display apparatus, the URI information is transmitted from the memory to the vital sign information display apparatus.

The electronic content includes information relevant to the vital sign information sensor.

According to one or more aspects of the present disclosure, there is provided a vital sign information display system.

The vital sign information display system comprises:
- a vital sign information sensor that acquires vital sign information from a physiological tissue of a subject; and
- a vital sign information display apparatus that is communicably connected to the vital sign information sensor.

The vital sign information sensor includes a sensor element configured to acquire the vital sign information from the subject, The vital sign information display apparatus is configured to:
- acquire the vital sign intimation from the sensor element;
- acquire an electronic content from a WEB server disposed on a communication network with reference to URI information that can gain access to the electronic content provided by the WEB server; and
- display the acquired electronic content.

When the vital sign information sensor is communicably connected to the vital sign information display apparatus, the vital sign information display apparatus acquires the electronic content from the WEB server with reference to the URI information.

The electronic content includes information relevant to the vital sign information sensor.

DESCRIPTION OF EMBODIMENTS

Figure 1:
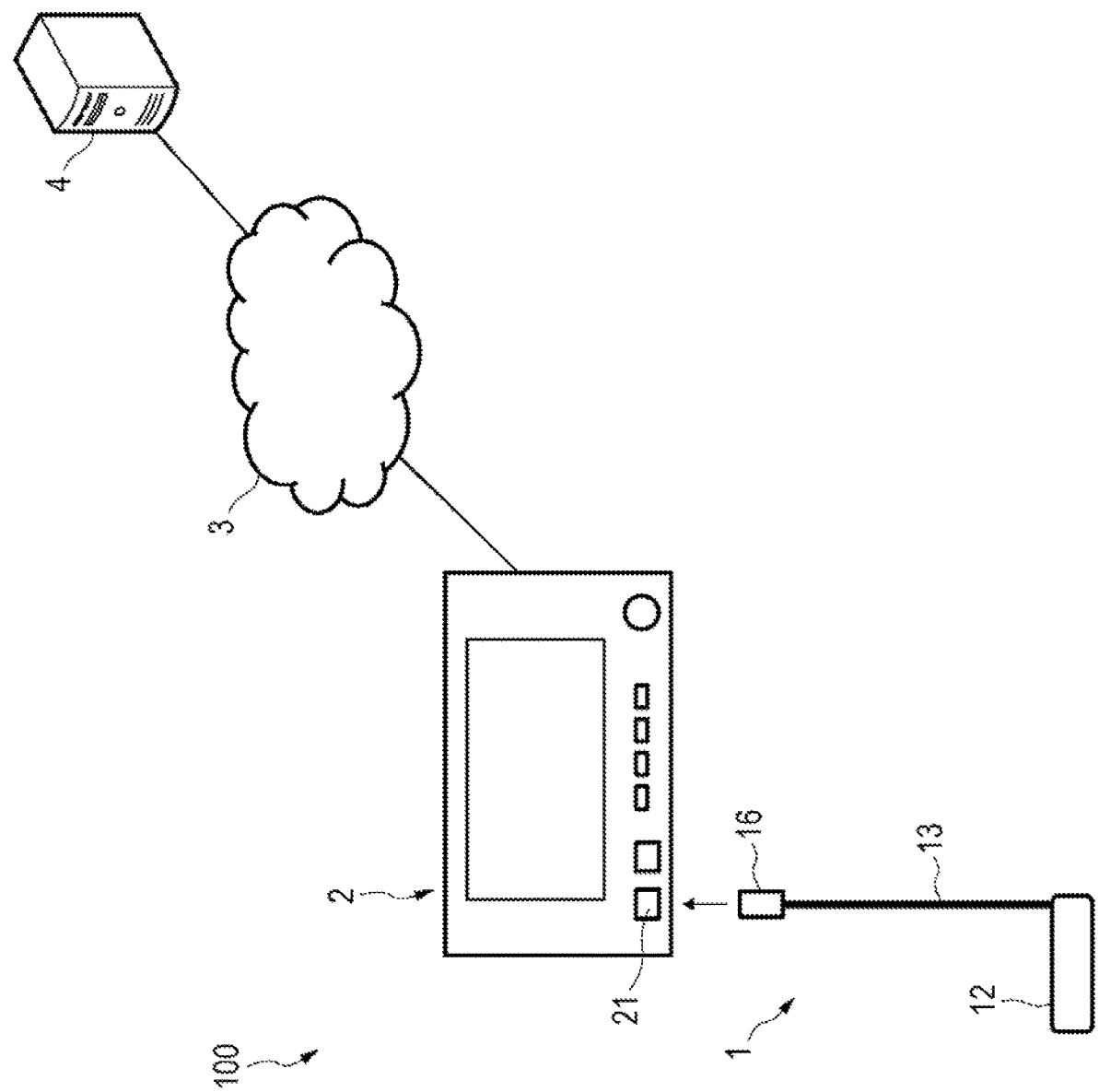
FIG. 1 is a schematic view showing a vital sign information display system according to an embodiment of the present invention (hereinafter referred to as present embodiment simply).

An embodiment of the present invention (hereinafter referred to as present embodiment) will be described below with reference to the drawings. FIG. 1 is a schematic view showing a vital sign information display system 100 according to the present embodiment. As shown in FIG. 1, the vital sign information display system 100 includes a vital sign information sensor 1 that is mounted on a physiological tissue (e.g. a finger etc.) of a subject (e.g., patient), and a vital sign information display apparatus 2 (hereinafter referred to as display apparatus 2) that is communicably connected to the vital sign information sensor 1. A pulse oximeter will be described as an example of the vital sign information sensor 1 in the present embodiment.

The vital sign information sensor 1 has a probe 12, a cable 13 and a connector 16. The probe 12 is, for example, wound around the finger of the subject to be thereby mounted on the finger of the subject. The cable 13 is configured so that the probe 12 and the connector 16 can be physically and electrically connected to each other through the cable 13.

When the connector 16 is inserted into a connector insertion portion 21 of the display apparatus 2, the vital sign information sensor 1 and the display apparatus 2 are physically and communicably connected to each other. Further, an electric signal outputted from the display apparatus 2 in a state in which the vital sign information sensor 1 and the display apparatus 2 in physically and communicably connected to each other is supplied to the probe 12 through the connector 16 and the cable 13.

The display apparatus 2 is configured to visually present vital sign information of the subject. The display apparatus 2 may be a special apparatus a vital sign information monitor) for displaying a trend graph of vital sign information of the subject or may be, for example, a personal computer, a work station, a smart phone, a tablet, or a wearable device (e.g. a smartwatch, an AR glass, or the like) that can be mounted on the body (e.g. an arm, the head, etc.) of a medical worker. In addition, the display apparatus 2 is communicably connected to a WEB server 4 through a communication network 3. The communication network 3 is constituted by at least one of the Internet, an LAN (Local Area Network) and a WAN (Wide Area Network). The WEB server 4 is disposed on the communication network 3 and configured to provide an electronic content of an HTML file (WEB page), a PDF file, an image file (e.g. a still image file and a moving image file, etc.) in accordance with an access request from a terminal. Particularly, the WEB server 4 is configured to transmit the electronic content including information relevant to the vital sign information sensor 1 (particularly, information relevant to an operating manual of the vital sign information sensor 1) to the display apparatus 2 in accordance with an access request from the display apparatus 2.

Figure 2:
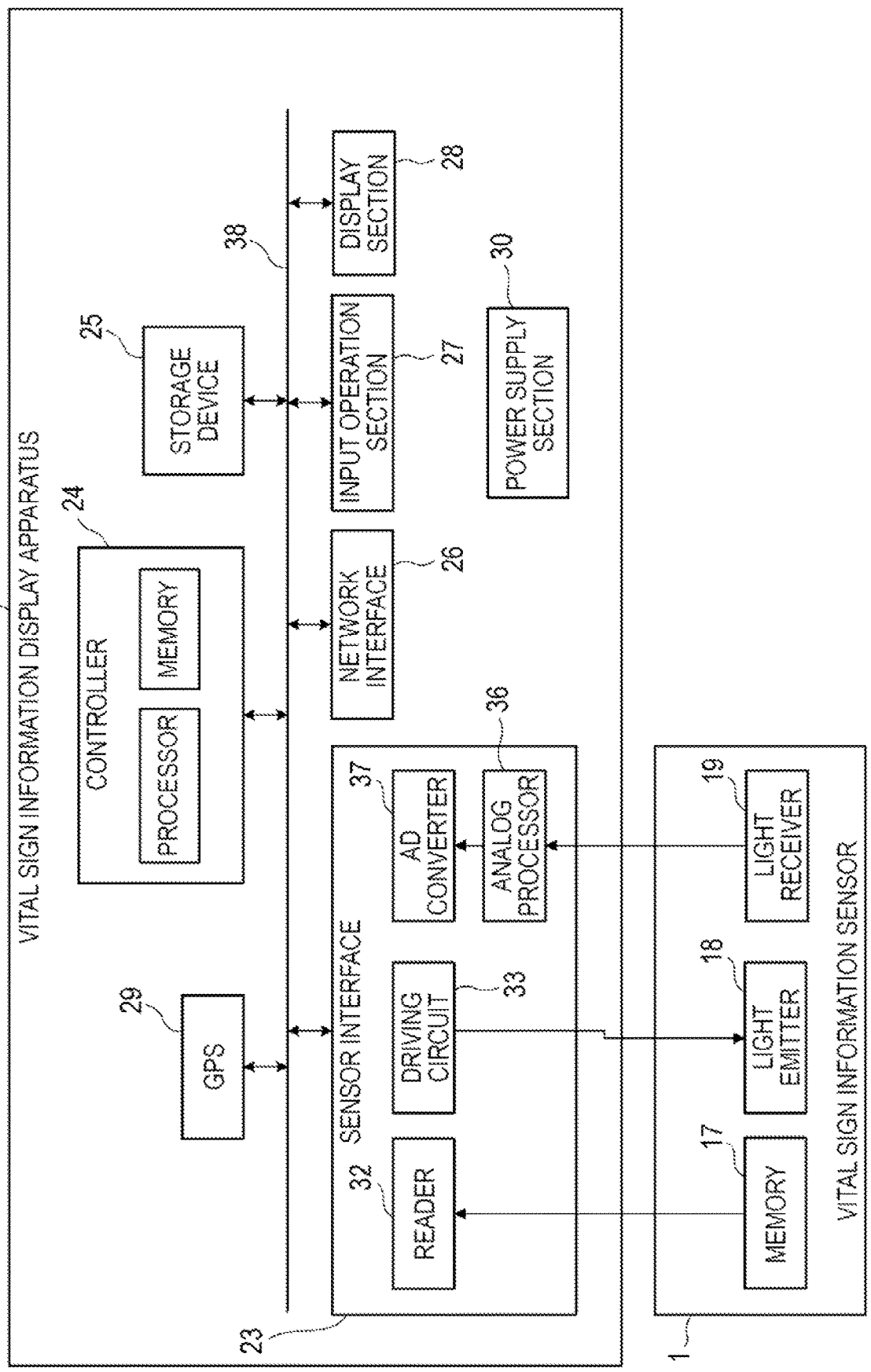
FIG. 2 is a view showing an example of hardware configurations of a pulse oximeter and a vital sign information display apparatus according to the present embodiment.

Next, hardware configurations of the vital sign information sensor 1 and the display apparatus 2 will be described below with reference to FIG. 2. FIG. 2 is a view showing an example of the hardware configurations of the vital sign information sensor 1 and the display apparatus 2. As shown in FIG. 2, the vital sign information sensor 1 includes a memory 17, a light emitter 18 and a light receiver 19.

The memory 17 is, for example, an ROM (Read Only Memory). URL (Uniform Resource Locator) information indicating a URL accessible to an electronic content provided by the WEB server 4 is stored in the memory 17. The URL is constituted by, for example, a communication protocol, a domain name, a directory name, and a file name. Incidentally, the URL may include an IF address of the WEB server 4 in place of the domain name. In addition, the URL information is stored as an example of URI (Uniform Resource Identifier) information in the memory 17 in the present embodiment. However, URN (Uniform Resource Name) information may be stored in the memory 17 in place of the URL information.

In addition, the memory 17 is disposed, for example, on the connector 16 of the vital sign information sensor 1. Specifically, the memory 17 may be mounted on a circuit board provided in the connector 16.

The light emitter 18 is disposed on the probe 12 of the vital sign information sensor 1, and configured to emit light toward the physiological tissue such as the finger of the subject. For example, the light emitter 18 has a red light LED configured to emit red light, and an infrared light LED configured to emit infrared light. The red light LED and the infrared light LED are driven and controlled to emit the red light and the infrared light alternately. For example, when a pulsed current supplied to the infrared light LED is at a high level, a pulsed current supplied to the red light LED is at a low level. On the other hand, when the pulsed current supplied to the infrared light LED is at a low level, the pulsed current supplied to the red light LED is at a high level.

The light receiver 19 is disposed on the probe 12 of the vital sign information sensor 1. The light receiver 19 is configured to receive light that is radiated from the light emitter 18 and transmitted through or reflected by the physiological tissue such as the finger of the subject, so that the light receiver 19 can generate a pulse wave signal (electric signal) indicating pulse waves. For example, the light receiver 19 is a photoelectric conversion element such as a PD (photodiode). The number of the light receivers 19 is not limited particularly. For example, when the light emitter 18 has the red light LED and the infrared light LED, the light receiver 19 has photosensitivity to the red light radiated from the red light LED and the infrared radiated from the infrared light LED. The light emitter 18 and the light receiver 19 function as a sensor element that is configured to acquire pulse wave information (an example of the vital sign information) relevant to the pulse waves of the subject. Additionally, the sensor element is not limited to the light emitter 18 and the light receiver 19. Type of the sensor element is not particularly limited as long as the sensor element is configured to acquire the vital sign information from the subject.

The red light is not absorbed very much by oxygenated hemoglobin (HbO2) contained in blood circulating in a blood vessel of the finger. On the other hand, the red light is absorbed very much by hemoglobin (Hb) contained in the blood. That is, when the blood contains a large amount of the oxygenated hemoglobin, a large quantity of the red light is transmitted through the finger and received by the light receiver 19. On the contrary, when the blood does not contain a large amount of the oxygenated hemoglobin, light intensity of the red light received by the light receiver 19 is small. Thus, the light intensity of the red light received by the light receiver 19 changes in accordance with a ratio of the oxygenated hemoglobin in the blood. On the other hand, the infrared light is not absorbed very much by the oxygenated hemoglobin and the hemoglobin. More specifically, there is no large difference between an absorption coefficient of the oxygenated hemoglobin for the infrared light and an absorption coefficient of the hemoglobin for the infrared light. Therefore, an SpO2 value of the subject can be calculated by use of a ratio between the light intensity of the red light received by the light receiver 19 and the light intensity of the infrared light received by the light receiver 19.

In addition, the display apparatus 2 includes a sensor interface 23, a controller 24, a storage device 25, a network interface 26, an input operation section 27, a display section 28, a UPS (Global Positioning System) 29 and a power supply section 30. These elements except the power supply section 30 are communicably connected to one another through a bus 38.

The sensor interface 23 is communicably connected to the vital sign information sensor 1. The sensor interface 23 includes a reader 32, a driving circuit 33, an analog processor 36, and an AD converter 37. The reader 32 is configured to acquire the URL information stored in the memory 17 when the vital sign information sensor 1 is communicably connected to the display apparatus 2. In other words, the UAL information is transmitted from the memory 17 to the reader 32. The driving circuit 33 is configured to control a driving current (pulsed current) supplied to the light emitter 18 based on a control signal outputted from the controller

24. For example, the driving circuit 33 is configured to control a timing of the pulsed current supplied to the red light LED and a timing of the pulsed current supplied to the infrared light LED.

The analog processor 36 is configured to amplify the pulse wave signal (a photoelectrically converted electric signal) outputted from the light receiver 19, and to filter a noise component (e.g. a high frequency component) of the amplified pulse wave signal. The AD converter 37 is configured to convert the pulse wave signal (analog signal) outputted from the analog processor 36 into a digital signal based on the control signal outputted from the controller 24.

The controller 24 has a processor and a memory. The processor includes at least one of a CPU (Central Processing Unit), a GPU (Graphics Processing Unit) and an MPU (Micro Processing Unit). The memory includes an RAM (Random Access Memory) and an ROM. The processor may be configured to develop a program designated from various programs incorporated into the storage device 25 or the ROM onto the RAM, and execute various processings in cooperation with the RAM.

The controller 24 is configured to control various operations of the display apparatus 2. In addition, the controller 24 can receive the digital signal of the pulse wave signal (hereinafter referred to as digital signal simply) from the AD converter 37, and acquire pulse wave data in which the digital signal and time information are associated with each other by use of a timer function of the processor. The pulse wave data have information about the intensities of the lights received by the light receiver 19, and the time information. The pulse wave data may include pulse wave data associated with the red light, and pulse wave data associated with the infrared light. The pulse wave data may be stored in the RAM or the storage device 25.

In addition, the controller 24 may generate SpO2 value data indicating a temporal change of the SpO2 value and/or pulse rate data indicating a temporal change of a pulse rate, based on the generated pulse wave data. The controller 24 can generate the SpO2 value data based on the pulse wave data associated with the red light and the pulse wave data associated with the infrared light. Thus, the controller 24 can acquire the pulse wave data, the SpO2 value data and/or the pulse rate data based on the digital signal outputted from the AD converter 37.

The storage device 25 is, for example, a storage device such as an HDD (Hard Disk Drive), an SSD (Solid State Drive), a flash memory, or the like. The storage device 25 is configured to store the programs or various data. For example, the pulse wave data, the SpO2 value data and/or the pulse rate data may be stored in the storage device 25.

The network interface 26 is configured to connect the display apparatus 2 to the communication network 3. Specifically, the network interface 26 may include various wired connection terminals for communicating with the WEB server 4 through the communication network 3. In addition, the network interface 26 may include various processing circuits and an antenna or the like for making wireless connection with an access point. A wireless communication standard between the display apparatus 2 and the access point is, for example, Wi-Fi (registered trademark), Bluetooth (registered trademark), ZigBee (registered trademark) or LPWA.

The display section 28 may be a display device such as a liquid crystal display or an organic EL display, or may be a display device such as a transmissive type or non-transmissive type head mount display mounted on the head of an operator. Further, the display section 28 may be a projector device projecting video onto a screen. The input operation section 27 is configured to accept an input operation of the medical worker operating the display apparatus 2 and to generate an instruction signal corresponding to the input operation. The input operation section 27 is, for example, a touch panel disposed to be superimposed on the display section 28, an operation button attached to a housing, a mouse and/or a keyboard, etc. After the instruction signal generated by the input operation section 27 is transmitted to the controller 24 through the bus 38, the controller 24 executes a predetermined operation in accordance with the transmitted instruction signal. The GPS 29 is configured to acquire position information (longitude, latitude) indicating a current position of the display apparatus 2. The power supply section 30 is configured to supply electric energy to the respective elements of the display apparatus 2.

Figure 3:
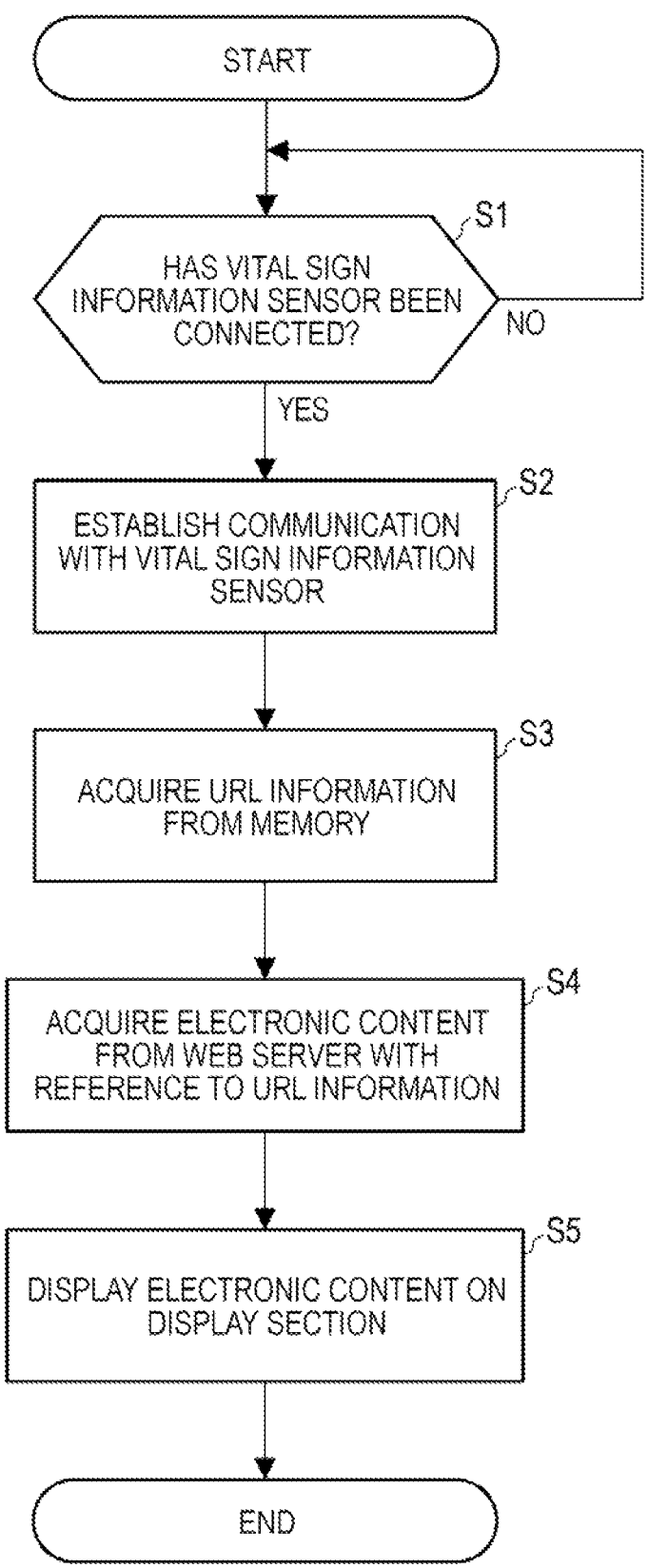
FIG. 3 is a flow chart for explaining an example of a method for visually presenting a medical worker with information relevant to an operating manual of the pulse oximeter.

Next, an example of a method for visually presenting a medical worker with information relevant to an operating manual of the vital sign information sensor 1 (an example of the information relevant to the vital sign information sensor 1) will be described with reference to FIG. 3. FIG. 3 is a flow chart for explaining the example of the method for visually presenting the medical worker with the information relevant to the operating manual of the vital sign information sensor 1.

In a step S1 as shown in FIG. 3, the controller 24 determines whether the vital sign information sensor 1 has been physically connected to the display apparatus 2 or not. Particularly, the controller 24 determines whether the connector 16 of the vital sign information sensor 1 has been inserted into the connector insertion portion 21 of the display apparatus 2 or not. When a result of the determination of the step S1 is NO, the controller 24 executes the determination processing of the step S1 again.

On the other hand, when the result of the determination of the step S1 is YES, the controller 24 establishes communication with the vital sign information sensor 1 (step S2). For example, to establish the communication with the vital sign information sensor 1, the controller 24 determines whether the connector 16 of the vital sign information sensor 1 physically connected to the display apparatus 2 is a connector of another medical device for acquiring vital sign information or not. Specifically, after the controller 24 in the display apparatus 2 has acquired information indicating the vital sign information sensor 1 from the memory 17, the controller 24 may refer to the acquired information to thereby determine whether the information indicates the vital sign information sensor 1 or the other medical device. The controller 24 may establish communication with the vital sign information sensor 1 when determining that the vital sign information sensor 1 is a pulse oximeter. On the other hand, the controller 24 may reject communication with the vital sign information sensor 1 when determining that the vital sign information sensor 1 is not a pulse oximeter.

Next, the controller 24 acquires URL information that can gain access to an electronic content provided by the WEB server 4 from the memory 17 through the reader 32 (step S3). In addition, in processing in and after the step S3, the controller 24 generates pulse wave data, SpO2 value data and/or pulse rate data based on a pulse wave signal after having acquired the pulse wave signal front the vital sign information sensor 1 (particularly the light receiver 19) through the sensor interface 23 in real time. The controller 24 displays a trend graph of the pulse wave data etc. on the display section 28. The trend graph displayed on the display section 28 may be updated in real time.

Next, in a step S4, the controller 24 refers to the URL information acquired from the memory 17 to thereby acquire an electronic content including information relevant to the operating manual of the vital sign information sensor 1 from the WEB server 4 that is disposed on the communication network 3 through the network interface 26. In this regard, firstly the controller 24 acquires an IP address of the WEB server 4 corresponding to a domain name of the URL information from a DNS server. Next, the controller 24 refers to the acquired IP address of the WEB server 4 to thereby transmit an access request of the electronic content to the WEB server 4. Next, the WEB server 4 transmits the electronic content to the display apparatus 2 in accordance with the access request of the electronic content issued from the display apparatus 2.

Here, the electronic content is a concept including an electronic file such as an HTML file, a PDF file, a moving image file, or the like. In addition, the information relevant to the operating manual of the vital sign information sensor 1 may be information indicating the operating manual of the vital sign information sensor 1, or may be information indicating a link to another electronic content (e.g. a PDF file etc.) indicating the operating manual. In this regard, when the acquired electronic content includes information indicating the link to the other electronic content indicating the operating manual, the medical worker designates the link through the input operation section 27 so that the display apparatus 2 can acquire the other electronic content indicating the operating manual from the WEB server 4.

Next, the controller 24 displays the electronic content acquired from the WEB server 4 on the display section 28 by use of a WEB browser (step S5). Thus, the information relevant to the operating manual of the vital sign information sensor 1 is visually provided to the medical worker through the display section 28.

According to the present embodiment, when the vital sign information sensor 1 is communicably connected to the display apparatus 2, the URL information is transmitted from the memory 17 to the display apparatus 2. Next, the display apparatus 2 can refer to the URL information to acquire the electronic content including the in formation relevant to the operating manual of the vital sign information sensor 1 from the WEB server 4 disposed on the communication network 3. Accordingly, even a medical worker who does not have much experience in using the vital sign information sensor 1 can check the information relevant to the operating manual of the vital sign information sensor 1 through the display section 28 of the display apparatus 2 (specially the WEB browser) without preliminarily preparing the prints etc. of the operating manual of the vital sign information sensor 1. Thus, it is possible to provide the vital sign information sensor 1 whose usability is improved, the display apparatus 2 and the vital sign information display system 100.

In addition, the electronic content acquired from the WEB server 4 may include information indicating operating manuals of the vital sign information sensor 1 written in a plurality of languages. For example, assume here that the electronic content includes an operating manual of the vital sign information sensor 1 written in Japanese and an operating manual of the vital sign information sensor 1 written in Chinese. In this case, a Japanese medical worker can browse the operating manual of the vital sign information sensor 1 written in Japanese, while a Chinese medical work can browse the operating manual of the vital sign information sensor 1 written in Chinese. Thus, any of the medical workers can browse the information relevant to the vital sign information sensor 1 in the plurality of languages through the display apparatus 2. Accordingly, it is possible to provide the vital sign information sensor 1 whose usability is improved, the display apparatus 2 and the vital sign information display system 100.

Figure 4:
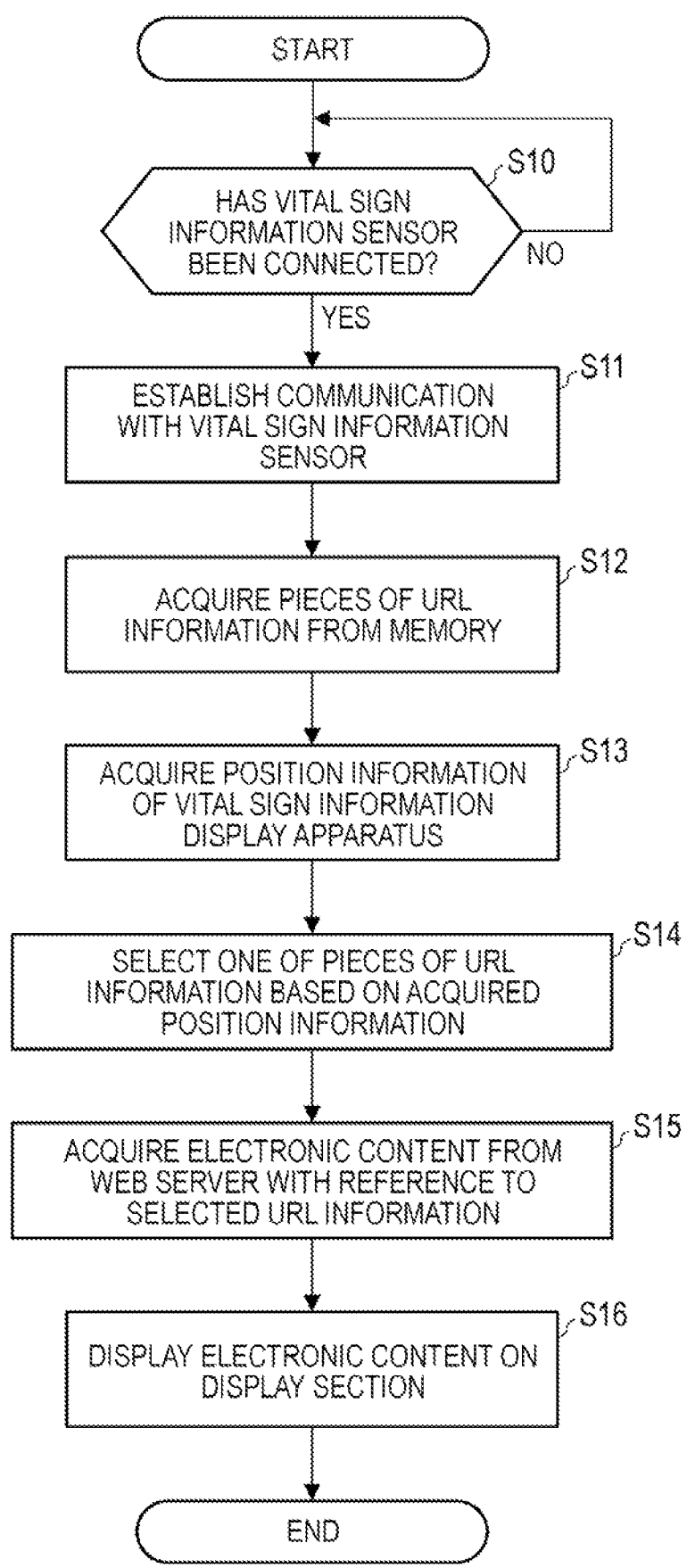
FIG. 4 is a flow chart for explaining another example of the method for visually presenting a medical worker with information relevant to an operating manual of the pulse oximeter.

Next, another example of the method for visually presenting a medical worker with information relevant to an operating manual of the vital sign information sensor 1 will be described with reference to FIG. 4. FIG. 4 is a flow chart for explaining the other example of the method for visually presenting the medical worker with the information relevant to the operating manual of the vital sign information sensor 1. This example is different from the method shown in FIG. 3 in that URL information which should be referred to is determined in accordance with position information of the display apparatus 2.

In a step S10 as shown in FIG. 4, the controller 24 determines whether the vital sign information sensor 1 has been physically connected to the display apparatus 2 or not. When a result of the determination of the step S10 is YES, the controller 24 establishes communication with the vital sign information sensor 1 (step S11). Next, the controller 24 acquires pieces of URL information from the memory 17 through the reader (step S12). Here, each of the pieces of URL information can gain access to a corresponding one of electronic contents. Further, each of the electronic contents includes information relevant to an operating manual of the vital sign information sensor 1 written in a corresponding one of languages. For example, assume here that the WEB server 4 has stored electronic contents A to C. In this case, here, the electronic content A includes an operating manual of the vital sign information sensor 1 written in Japanese. The electronic content B includes an operating manual of the vital sign information sensor 1 written in English. The electronic content C includes an operating manual of the vital sign information sensor 1 written in Chinese. In this case, a piece of URL information that can gain access to the electronic content A, a piece of URL information that can gain access to the electronic content B, and a piece of URL information that can gain access to the electronic content C may be also stored in the memory 17. In addition, each of the pieces of URL information is associated with a corresponding one of the official languages. That is, each of the pieces of URL information has a piece of metadata indicating a corresponding official language. For example, the piece of URL information that can gain access to the electronic content B has a piece of metadata indicating English as the official language.

Next, the controller 24 acquires position information of the display apparatus 2 by use of the GPS 29 (step S13). Then, the controller 24 selects one of the pieces of URL information acquired from the memory 17 based on the acquired position information of the display apparatus 2 (step S14). In this regard, the controller 24 specifies an official language used in a region (e.g. a country etc.) where the display apparatus 2 is currently positioned, based on the position information of the display apparatus 2. Next, the controller 24 refers to the respective pieces of metadata for the pieces of URL information to select one piece of URL information associated with the specified official language from the pieces of URL information. For example, assume that the display apparatus 2 is currently positioned in the USA. In this case, the controller 24 specifies the official language as English based on the position information of the display apparatus 2. Next, the controller 24 refers to the respective pieces of metadata for the pieces of URL information to thereby select one piece of URL information associated with English from the pieces of information.

Next, the controller 24 refers to the selected piece of URL information to thereby acquire an electronic content corresponding to the selected piece of URL information from the WEB server 4 disposed on the communication network 3 through the network interface 26 (step S15). In other words, the controller 24 acquires an electronic content including information relevant to the operating manual of the vital sign information sensor 1 written in the official language corresponding to the position information of the display apparatus 2 from the WEB server 4. For example, the controller 24 refers to the piece of URL information associated with English to thereby acquire an electronic content including the information relevant to the operating manual written in English.

Then, the controller 24 displays the electronic content acquired from the WEB server 4 on the display section 28 by use of the WEB browser (step S16). Thus, the information relevant to the operating manual of the vital sign information sensor 1 written in the official language corresponding to the position information of the display apparatus 2 is visually provided to the medical worker through the display section 28.

According to the present embodiment, after one of the pieces of URL information has been selected based on the position information of the display apparatus 2, the electronic content corresponding to the selected piece of URL information is acquired. Thus, the medical worker can check the information relevant to the operating manual of the vital sign information sensor 1 in the language associated with the position information of the display apparatus 2 through the display apparatus 2. For example, assume that the medical worker operating the display apparatus 2 is in the USA. In this case, the medical worker can check the operating manual written in English that is the official language of the USA. Accordingly, it is possible to provide the vital sign information sensor 1 whose usability is improved, the display apparatus 2 and the vital sign information display system 100.

Incidentally, in the example, the controller 24 acquires the position information of the display apparatus 2 by use of the GPS 29. However, the controller 24 may acquire the position information of the display apparatus 2 based on an IP address of the display apparatus 2 in place of the GPS 29. In this case, the controller 24 can at least specify the region (e.g. the country etc.) where the display apparatus is currently positioned based on the IP address of the display apparatus 2. Accordingly, the controller 24 can specify the official language used in the region where the display apparatus 2 is currently positioned.

In addition, the example of the method for visually presenting the medical worker with the information relevant to the operating manual of the vital sign information sensor as an example of the information relevant to the vital sign information sensor 1 has been described in the present embodiment. However, the present embodiment is not limited thereto. For example, the information relevant to the vital sign information sensor 1 may include at least one of i) the information relevant to the operating manual of the vital sign information sensor 1, ii) information relevant to specifications of the vital sign information sensor 1, iii) information relevant to a pamphlet of the vital sign information sensor 1, and iv) information relevant to the subject to which the vital sign information sensor 1 is attached. In this case, the electronic content acquired from the WEB server 4 may include at least one of the aforementioned pieces of information i) to iv).

Further, in the description of the present embodiment, the display apparatus 2 acquires the URL information from the memory 17 of the vital sign information sensor 1 after establishing communication with the vital sign information sensor 1. However, the present embodiment is not limited thereto. For example, the URL information may be stored in the memory of the controller 24 or the storage device 25. In this case, after establishing communication with the vital sign information sensor 1, the controller 24 may refer to the URL information stored in the memory of the controller 24 or the storage device 25 so that the controller 24 can acquire the electronic content from the WEB server 4. Further, the controller 24 may select one of the pieces of URL information stored in the memory of the controller 24 or the storage device 25 based on the position information of the display apparatus 2 after acquiring the position information of the display apparatus 2.

In addition, the vital sign information sensor 1 has been described as an example of the vital sign information sensor in the present embodiment. However, the kind of the vital sign information sensor is not limited to the pulse oximeter. For example, an electrocardiogram (ECG) sensor acquiring electrocardiogram information of the subject, a CO2 sensor, a blood pressure measurement cuff, an electroencephalograph electrode, a body temperature measurement probe, or the like, may be used as a vital sign information sensor in place of the pulse oximeter. In addition, each of such vital sign information sensors may be a non-contact sensor which does not have to be mounted on the subject.

Although the embodiment of the present invention has been described above, the technical scope of the present invention should not be interpreted limitedly by the description of the present embodiment. It should be understood by those skilled in the art that the present embodiment is merely exemplified but various changes can be made on the embodiment within the scope of the claimed inventions. The technical scope of the present invention should be determined based on the scope of the claimed inventions and the scope of equivalents thereof.

This application is based on Japanese Patent Application No. 2018-064878 filed on Mar. 29, 2018, the entire contents of which are incorporated herein by reference.

The invention claimed is:

1. A vital sign information sensor for acquiring vital sign information from a physiological tissue of a subject, the sensor comprising:
   a sensor element configured to acquire the vital sign information from the subject; and
   a memory storing pieces of URI information, wherein the pieces of URI information are capable of gaining access to an electronic content provided by a WEB server disposed on a communication network;
   wherein the vital sign information sensor is configured to communicably connect to a vital sign information display apparatus;
   wherein the information display apparatus is configured to determine whether the vital sign information sensor is communicably connected to the vital sign information display apparatus and acquire position information of the vital sign information display apparatus;
   wherein the vital sign information sensor is configured to, in response to the vital sign information display apparatus determining that the vital sign information sensor is communicably connected to the vital sign information display apparatus, select one of the pieces of URI information based on the acquired position information of the vital sign information display apparatus, and automatically transmit the selected one of the pieces of URI information from the memory to the vital sign information display apparatus, and wherein the electronic content includes information corresponding to the vital sign information sensor.

2. The vital sign information sensor according to claim 1, wherein the information corresponding to the vital sign information sensor includes information relevant to an operating manual of the vital sign information sensor.

3. The vital sign information sensor according to claim 1, wherein:
the information corresponding to the vital sign information sensor includes:
first information corresponding to the vital sign information sensor written in a first language; and
second information corresponding to the vital sign information sensor written in a second language different from the first language.

4. The vital sign information sensor according to claim 3, wherein:
the electronic content includes:
a first electronic content that includes the information corresponding to the vital sign information sensor written in the first language; and
a second electronic content that includes the information corresponding to the vital sign information sensor written in the second language; and
the pieces of URI information include:
first URI information that can gain access to the first electronic content; and
second URI information that can gain access to the second electronic content.

5. The vital sign information sensor according to claim 1, wherein
when the vital sign information sensor is physically connected to the vital sign information display apparatus, the pieces of URI information are transmitted from the memory to the vital sign information display apparatus.

6. The vital sign information sensor according to claim 1, wherein the vital sign information sensor and the vital sign information display apparatus are physically separated.

7. A vital sign information sensor for acquiring vital sign information from a physiological tissue of a subject, the sensor comprising:
a sensor element configured to acquire the vital sign information from the subject; and
a memory storing pieces of URI information, wherein the pieces of URI information are capable of gaining access to an electronic content provided by a WEB server disposed on a communication network;
wherein the vital sign information sensor is configured to communicably connect to a vital sign information display apparatus;
wherein the information display apparatus is configured to determine whether the vital sign information sensor is communicably connected to the vital sign information display apparatus and acquire position information of the vital sign information display apparatus;
wherein the vital sign information sensor is configured to, in response to the vital sign information display apparatus determining that the vital sign information sensor is communicably connected to the vital sign information display apparatus, select one of the pieces of URI information based on the acquired position information of the vital sign information display apparatus, and automatically transmit the selected one of the pieces of URI information from the memory to the vital sign information display apparatus, wherein the electronic content includes information corresponding to the vital sign information sensor;

wherein the vital sign information sensor is a pulse oximeter; and wherein the sensor element includes:
a light emitter configured to emit light toward the physiological tissue of the subject; and
a light receiver configured to receive the light that is emitted from the light emitter and then transmitted through or reflected by the physiological tissue.

8. A vital sign information display system comprising:
a vital sign information sensor configured to acquire vital sign information from a physiological tissue of a subject; and
a vital sign information display apparatus configured to communicably connect to the vital sign information sensor,
wherein the vital sign information sensor includes a sensor element configured to acquire the vital sign information from the subject,
wherein the vital sign information display apparatus is configured to:
determine whether or not the vital sign information sensor is communicably connected to the vital sign information display apparatus;
acquire position information of the vital sign information display apparatus;
acquire the vital sign information from the sensor element;
in response to determining that the vital sign information sensor is communicably connected to the vital sign information display apparatus, automatically acquire an electronic content from a WEB server disposed on a communication network with reference to pieces of URI information that can gain access to the electronic content provided by the WEB server; and
display the acquired electronic content,
wherein the electronic content includes information corresponding to the vital sign information sensor;
wherein the vital sign information sensor is configured to, in response to the vital sign information display apparatus determining that the vital sign information sensor is communicably connected to the vital sign information display apparatus, select one of the pieces of URI information based on the acquired position information of the vital sign information display apparatus, and automatically transmit the selected one of the pieces of URI information from the memory to the vital sign information display apparatus.

9. The vital sign information display system according to claim 8,
wherein the vital sign information sensor further includes a memory storing the pieces of URI information, and
wherein in response to determining that the vital sign information sensor, that the vital sign information sensor is communicably connected to the vital sign information display apparatus, the vital sign information display apparatus is configured to automatically acquire the pieces of URI information from the memory and then automatically acquire the electronic content from the WEB server with reference to the acquired pieces of URI information.

10. The vital sign information display system according to claim 8, wherein:
   the electronic content includes electronic contents;
   each of the electronic contents includes the information corresponding to the vital sign information sensor written in a different language;
   each of the pieces of URI information can gain access to a corresponding one of the electronic contents, and
   wherein the vital sign information display apparatus is configured to:
   acquire an electronic content corresponding to the selected one of the pieces of URI information from the WEB server with reference to the selected one of the pieces of URI information; and
   display the acquired electronic content.

* * * * *